United States Patent
Bruce et al.

(10) Patent No.: US 6,604,609 B2
(45) Date of Patent: Aug. 12, 2003

(54) SYSTEM FOR SELECTING FEMININE HYGIENE PRODUCTS

(75) Inventors: Anne Holland Bruce, Cincinnati, OH (US); Gale Jenkins Fogg, Cincinnati, OH (US); Frances Jeanne Diedling, Cincinnati, OH (US); John Lee Hammons, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 10/300,281

(22) Filed: Nov. 20, 2002

(65) Prior Publication Data

US 2003/0097109 A1 May 22, 2003

Related U.S. Application Data

(60) Provisional application No. 60/331,975, filed on Nov. 21, 2001.

(51) Int. Cl.[7] .............................. A41B 9/12; A61F 13/15
(52) U.S. Cl. .............................. 186/52; 283/60.1
(58) Field of Search .................. 186/52, 35; 604/358; 40/545, 358, 584; 283/56, 36, 41, 60.1; 434/395; 2/406; 223/1

(56) References Cited

U.S. PATENT DOCUMENTS

| 5,558,663 A | 9/1996 | Weinberger et al. |
|---|---|---|
| 5,584,829 A | 12/1996 | Lavash et al. |
| 5,683,373 A | 11/1997 | Darby |
| 5,714,098 A * | 2/1998 | Potter .................. 264/40.1 |
| 2003/0057025 A1 * | 3/2003 | Cagner .................. 186/52 |

FOREIGN PATENT DOCUMENTS

| WO | WO 98/51249 A1 | 11/1998 |
| WO | WO 00/59426 A1 | 10/2000 |
| WO | WO 00/72790 A1 | 12/2000 |
| WO | WO 01/35887 A1 | 5/2001 |
| WO | WO 01/35891 A1 | 5/2001 |

* cited by examiner

Primary Examiner—Donald P. Walsh
Assistant Examiner—Mark J Beauchaine
(74) Attorney, Agent, or Firm—Eileen L. Hughett; Ken K. Patel; Steven W. Miller (57) ABSTRACT

A method of providing a system of selecting feminine hygiene products to a consumer comprises the steps of: providing an array of feminine hygiene products from at least one array, wherein said array is comprised of one or more feminine hygiene products and wherein said array is adapted to correspond to a predetermined range of panty styles, and; providing information to said consumer regarding the products which make up said array, thereby enabling said consumer to select feminine hygiene products by panty style. A kit for use with the system of selecting feminine hygiene products comprises at least one feminine hygiene product, a package containing the product and indicia on the package to inform the consumer of a panty style with which said product is to be used.

10 Claims, 8 Drawing Sheets

SYSTEM FOR SELECTING FEMININE HYGIENE PRODUCTS

This application claims benefit of provisional application No. 60/331,975 filed Nov. 21, 2001.

FIELD OF THE INVENTION

The present invention relates to a method of providing a system of selecting feminine hygiene products to a consumer.

BACKGROUND OF THE INVENTION

Absorbent hygiene products, such as sanitary napkins, panty liners, and incontinence pads, are devices that are typically worn in the crotch area of an undergarment. These devices are designed to absorb and retain liquid and other discharges from the human body and to prevent soiling of the wearer's body and clothing. Sanitary napkins and panty liners are types of absorbent articles worn by women. A wide variety of shapes and dimensions of such articles are currently used by women for the collection of menses and other bodily discharges.

Current methods of marketing absorbent articles as feminine protection products include systems differentiated by absorbency levels (light flow, moderate flow, heavy flow), special needs (overnight, teens), area coverage (length, width, wings), and thickness (regular, ultra thin). These current methods can cause confusion for the consumer and do not lend themselves to fashion or femininity, both of which are important to female consumers.

One problem not addressed in the prior art relates to the wide variations in styles of panties. As protection of panties from soiling by body fluids is a primary function of feminine hygiene products, the problems of both protection and aesthetics in relation to "force fitting", for example, the same sanitary napkin style, into a number of panty styles has gone unresolved.

Feminine hygiene products specifically designed to be worn with thong undergarments are known in the art. The chief design consideration for such articles is the narrow dimension of the rear portion of thong undergarments. However, as will be shown below, other currently marketed panties can be better protected by feminine hygiene products designed to match their dimensions.

BACKGROUND ART

The following references relate to absorbent structures: U.S. Pat. No. 5,558,663, issued Sep. 24, 1996, in the names of Weinberger et al.; U.S. Pat. No. 5,584,829, issued Dec. 17, 1996, in the names of Lavash et al.; U.S. Pat. No. 5,683,373, issued Nov. 4, 1997, in the name of Darby; PCT Pat. Publication WO 98/51249, published Nov. 19, 1998, in the name of Van Der Meulen; PCT Pat. Publication WO 00/59426, published Oct. 12, 2000, in the name of Castellana; PCT Pat. Publication WO 00/72790, published Dec. 7, 2000, in the name of Persson; PCT Pat. Publication WO 01/35891, published May 25, 2001 in the names of Drevik et al.; and PCT Pat. Publication WO 01/35887, published May 25, 2001, in the name of Persson.

SUMMARY OF THE INVENTION

The present invention relates to a method of selecting among systems of feminine hygiene products by a consumer. The method comprises providing a system of selecting feminine hygiene products to a consumer, the method comprising the steps of: providing an array of feminine hygiene products from at least one array, wherein said array is comprised of one or more feminine hygiene products and wherein said array is adapted to correspond to a predetermined range of panty styles, and, providing information to the consumer regarding the products which make up the array, thereby enabling said consumer to select feminine hygiene products by panty style.

This invention also relates to a method of selecting feminine hygiene products by a consumer, comprising the steps of: viewing information regarding at least one array of feminine hygiene products, wherein said array is comprised of one or more feminine hygiene products and wherein said array is adapted to correspond to a predetermined range of panty styles, and selecting feminine hygiene products by panty style.

Other optional parameters could be incorporated into either method as desired including, but not limited to pre-determined ranges of one or more of the following: body size, absorbency levels, area coverage and thickness/body fit.

The present invention also relates to a kit comprising the absorbent articles, as described above, packaging containing the absorbent articles, and indicia on the package to inform the purchaser of those panty styles with which the article may suitably be used. The indicia used can be in the form of photographs. Without being limited to those panties listed, the panty styles, with which the absorbent article is used, can be selected from the group consisting of: a) thong panties, b) high leg cut panties (also known as French cut panties), c) hipsters, d) bikini panties and e) briefs.

DETAILED DESCRIPTION OF THE INVENTION

Figure 8:
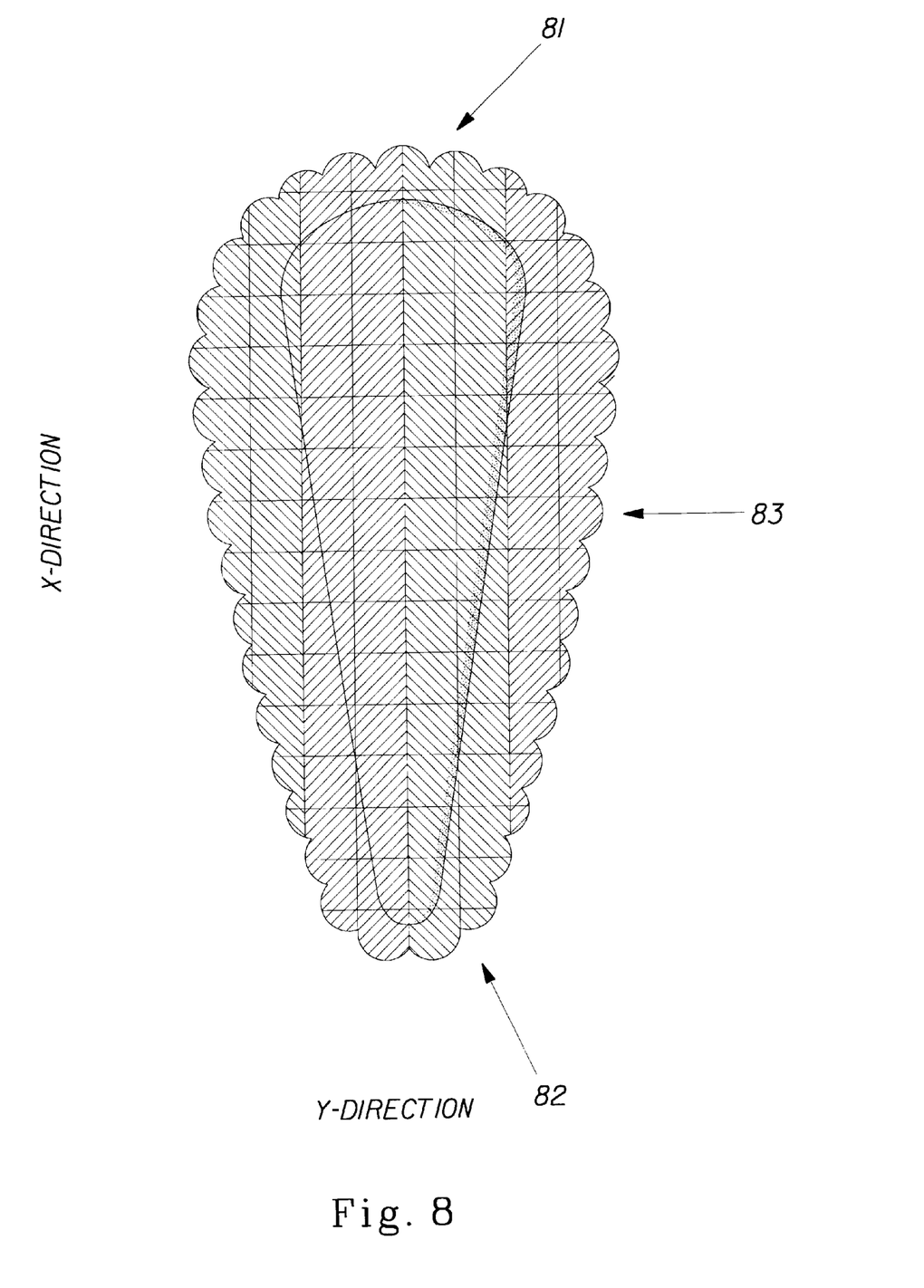
FIG. 8 illustrates a top plan view of a sanitary napkin, designed to be worn with a thong panty.
Figure 9:
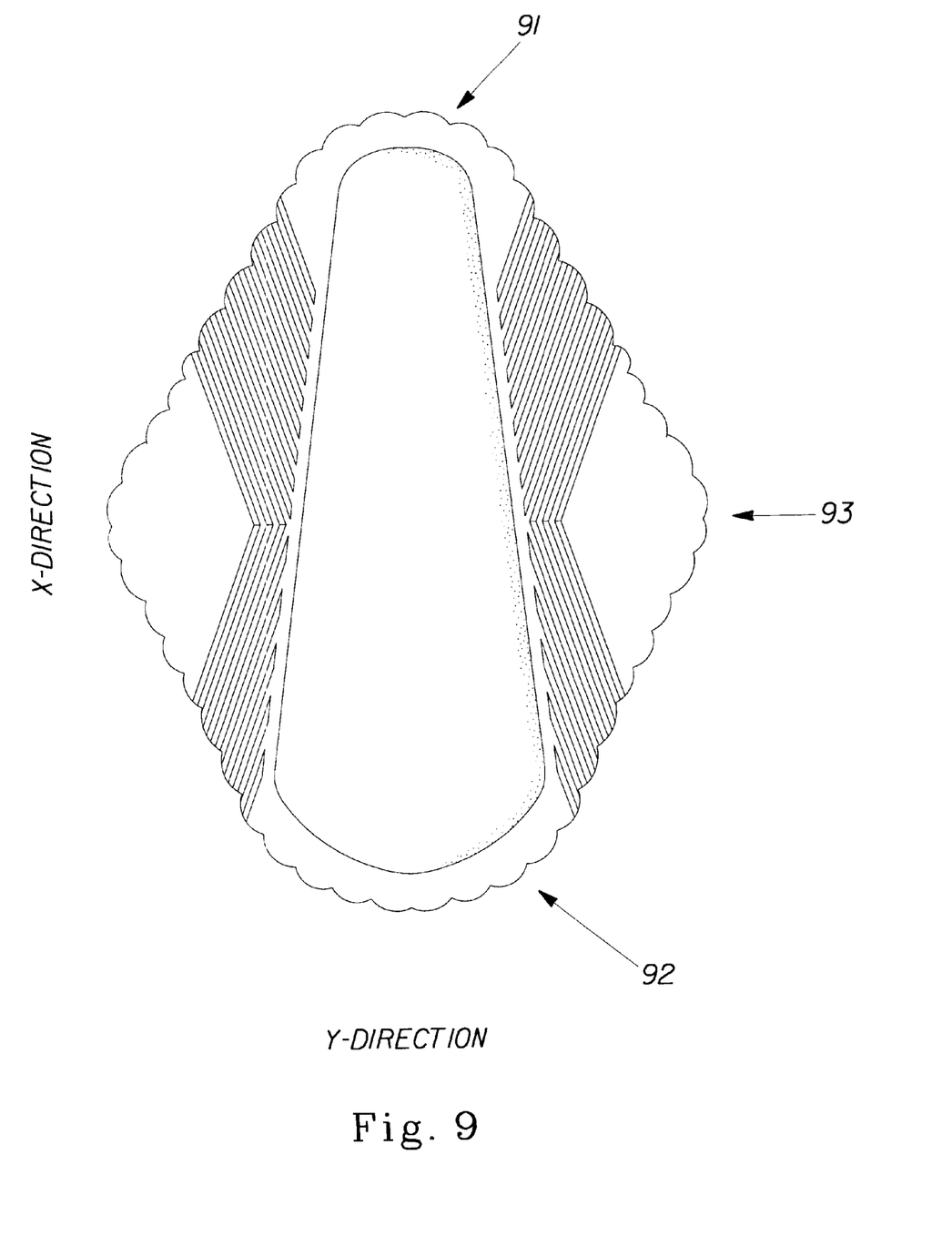
FIG. 9 illustrates a top plan view of a sanitary napkin, designed to be worn with a bikini panty.
Figure 10:
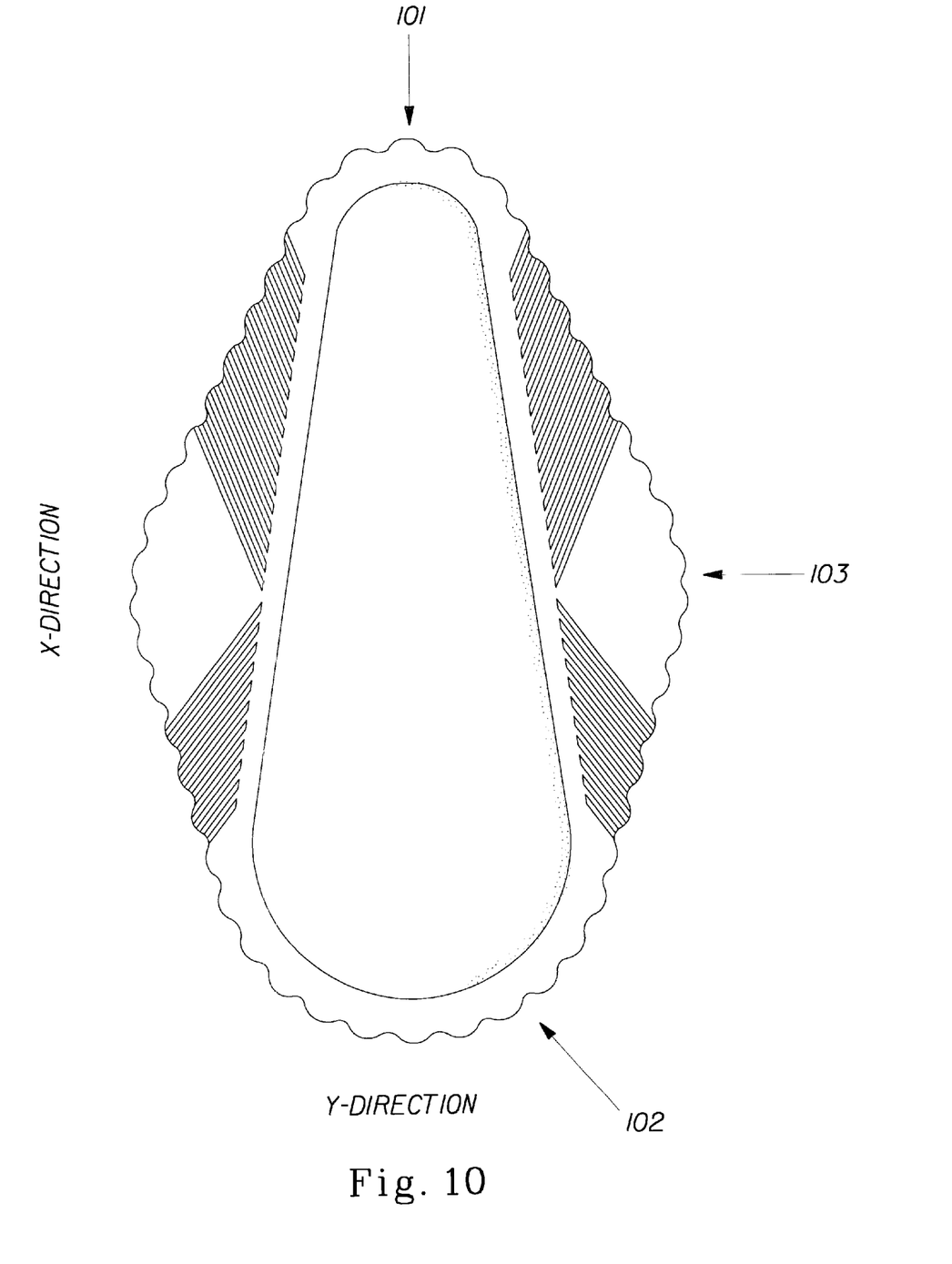
FIG. 10 illustrates a top plan view of a sanitary napkin, designed to be worn with a high cut panty.

The "x" and "y" directions utilized in the "XY pattern" of the embossments and apertures of the instant articles are defined as follows. The absorbent article has a longitudinal centerline L which runs along the "x" axis, as shown in FIGS. 8, 9, and 10. The term "longitudinal" as used herein refers to a line, axis or direction in the plane of the absorbent article that is generally aligned with (e.g., approximately parallel to) a vertical plane which bisects a standing wearer into left and right body halves when the absorbent article is worn. The "length" of the absorbent article is the linear measurement of the absorbent article in the x-direction. The transverse, lateral or "y direction", as used herein, refers to a line, axis or direction that is generally perpendicular to the longitudinal direction. The lateral direction is shown in FIGS. 4, 8, 9, and 10 as the "y" direction. The "width" of the absorbent article is the linear measurement of the absorbent article taken in the y-direction.

As used herein the "z" direction, shown in FIG. 4, is a direction parallel to the vertical plane described above and shown in FIG. 4.

As used herein "upper" refers to an orientation in the z-direction toward the wearer's head.

As used herein "lower" or downwardly refers to an orientation in the z-direction toward the wearer's feet.

As used herein the "height" of the absorbent article is the linear measurement of the absorbent article taken in the z-direction.

Figure 1:
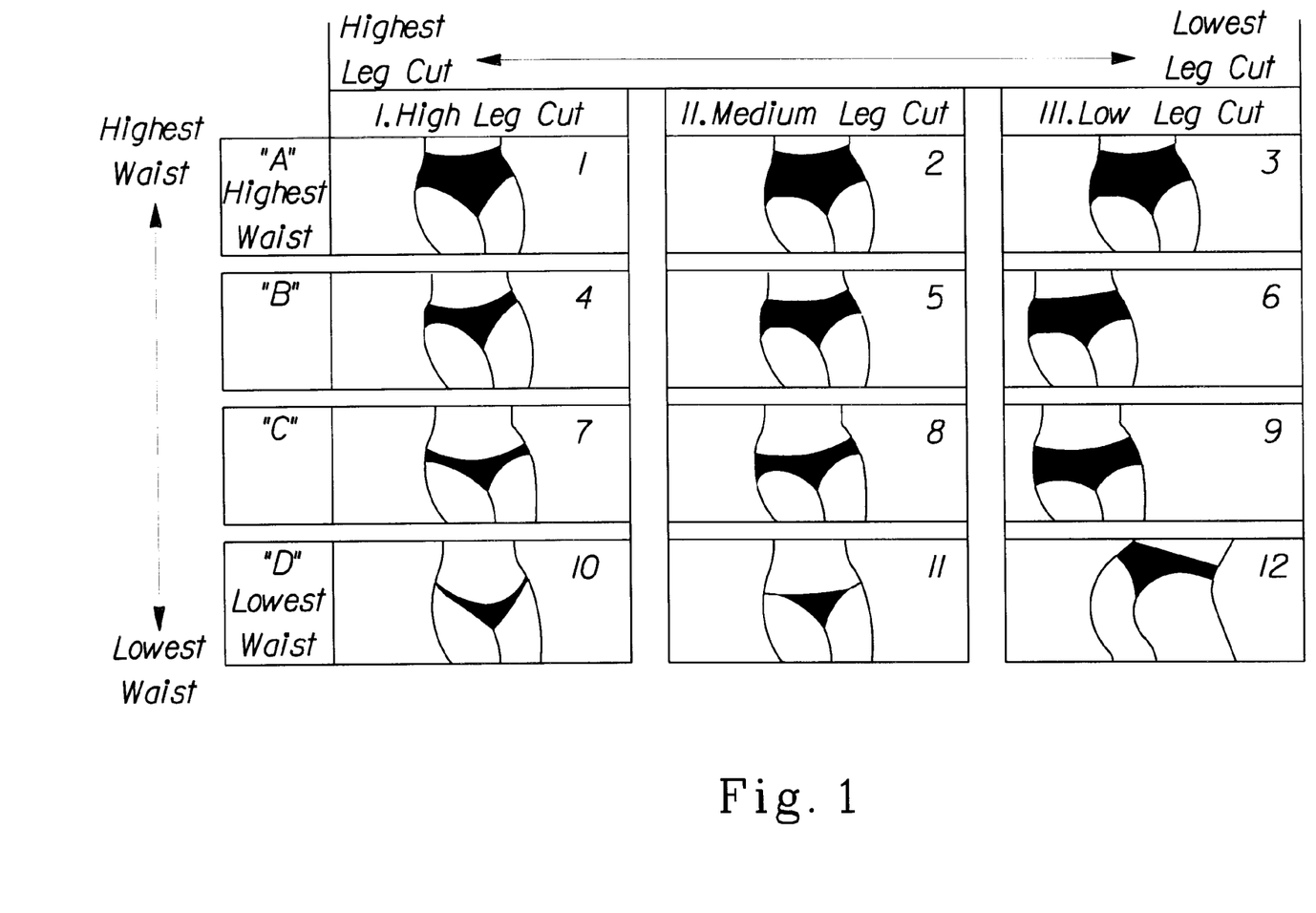
FIG. 1 illustrates panty design showing existing designs as a function of leg cut and waist height.

Disclosed herein is a system of feminine protection products designed for and selected by the consumer on the basis of panty styles. There are numerous ways to characterize or categorize panty styles. FIG. 1 is a drawing that provides such a characterization as a function of leg cut and waist height. The first row of panties, which is labeled "A", all have high waists, while their leg cuts become progressively lower as the chart moves to the right. Rows "B", "C", and "D" each show panties with a progressively lower waist cut, while the height of the leg cut becomes lower to the right. Future panty designs may have dimensions between those shown. Other considerations include panty crotch dimensions and curvatures, materials used, etcetera.

Preferred embodiments of the absorbent articles, chosen from the instant systems, are possible because selection of specific newly available absorbent materials, combinations of these absorbent materials and configuration of these materials, allows body fluids delivered to the center of a topsheet to be moved quickly and easily, not only into the interior of the absorbent core but also outward to the periphery of the napkin, where they can be securely stored. Such performance allows the design of sanitary napkins to be based on physical measurements of specific panty styles for improved fit, comfort and aesthetics, while maintaining excellent absorbency.

Regardless of the panty styles on the market at any given time, a system of selecting feminine hygiene products, based on a predetermined range of panty styles, enables a consumer to quickly and accurately determine which feminine hygiene product will provide optimum fit.

Below is a chart illustrating five styles of panties, categorized by 1) crotch dimensions taken at three places in the crotch area of the panty (minimum crotch width, front crotch width and back crotch width, 2) rise, 3) side seam width and 4) leg cut. The front and back crotch width was measured 90 mm from minimum crotch width. While the five styles illustrated below are among the most widely distributed, other variations are currently marketed.

|  | Style A | Style B | Style C | Style D | Style E |
| --- | --- | --- | --- | --- | --- |
| Minimum Crotch Width, mm | | | | | |
| Average/St Dev | 55 | 67/8 | 66/8 | 70/8 | 69/9 |
| Range | 47–68 | 55–83 | 52–78 | 56–90 | 48–85 |
| Front* Crotch Width, mm | | | | | |
| Average | 115 | 133/24 | 149/32 | 130/15 | 175/36 |
| Range | 102–150 | 89–198 | 109–210 | 96–160 | 127–250 |
| Back* Crotch Width, mm | | | | | |
| Average | 28 | 170/28 | 191/44 | 170/32 | 188/47 |
| Range | 24–37 | 125–222 | 120–290 | 103–295 | 124–320 |
| Rise, mm | | | | | |
| Average | Not | 239/17 | 256/17 | 299/23 | 336/33 |
| Range | Available | 270–210 | 225–295 | 250–350 | 220–413 |
| Side Seam Width, mm | | | | | |
| Average | Not | 53/18 | 91/28 | 74/17 | 205/34 |
| Range | Available | 25–81 | 35–130 | 40–105 | 133–278 |
| Leg Cut, mm | | | | | |
| Average | 272 | 186/24 | 165/32 | 225/21 | 134/38 |
| Range | 213–329 | 238–140 | 120–230 | 172–280 | 70–255 |

Variation in feminine hygiene product design in the past was based on body size and/or the level of absorbency, which was required to prevent body exudates from leaking onto the wearer's garments. The sanitary napkin design embodiments disclosed by this specification are, primarily, based on the design of the wearer's panty. For example, both absorbent core and wing shape and dimensions are contoured to the panty crotch dimensions.

Figure 3:
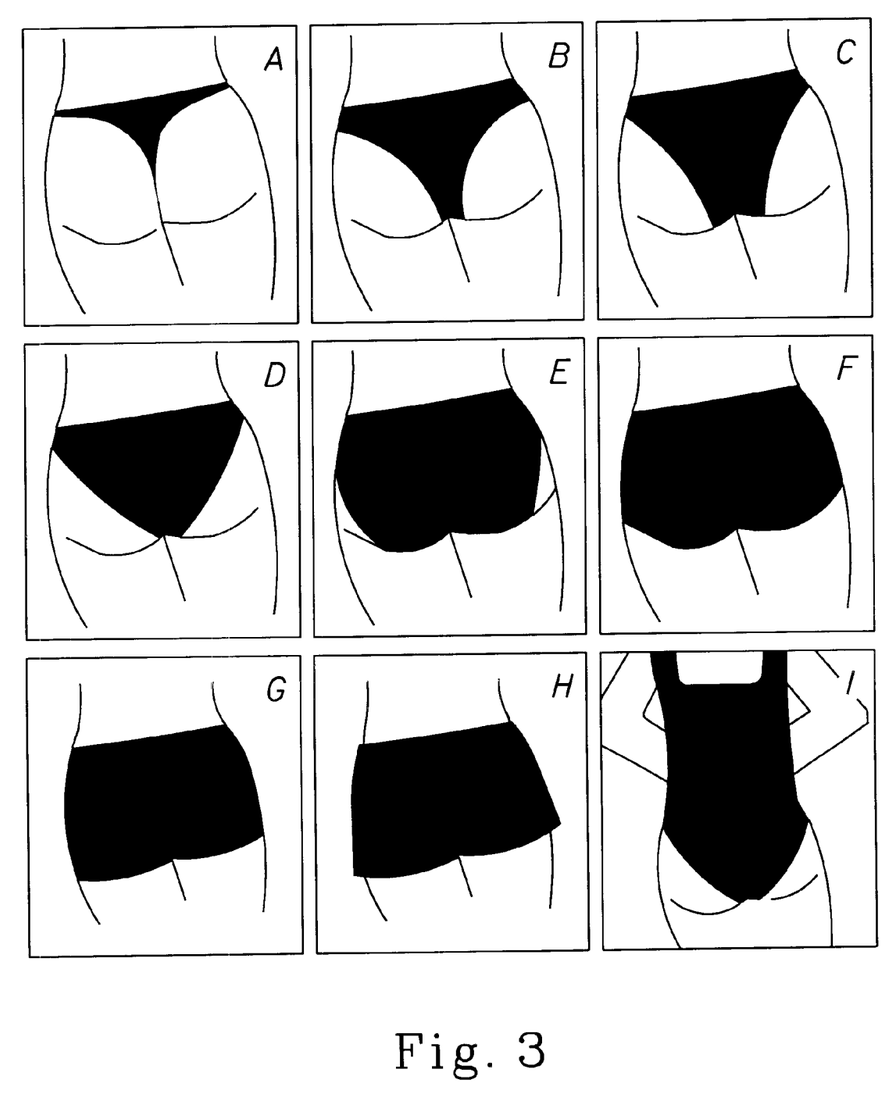
FIG. 3 shows back views of currently marketed panty styles. Panty A is a thong. Panties B and C are high leg cut variations marketed in Latin America. Panties D and E are high leg cut panties. Panty F is a brief. Panty G is a "modern" or "boy" brief. Panty H is a tap pant. Panty I is a body suit.
Figure 4:
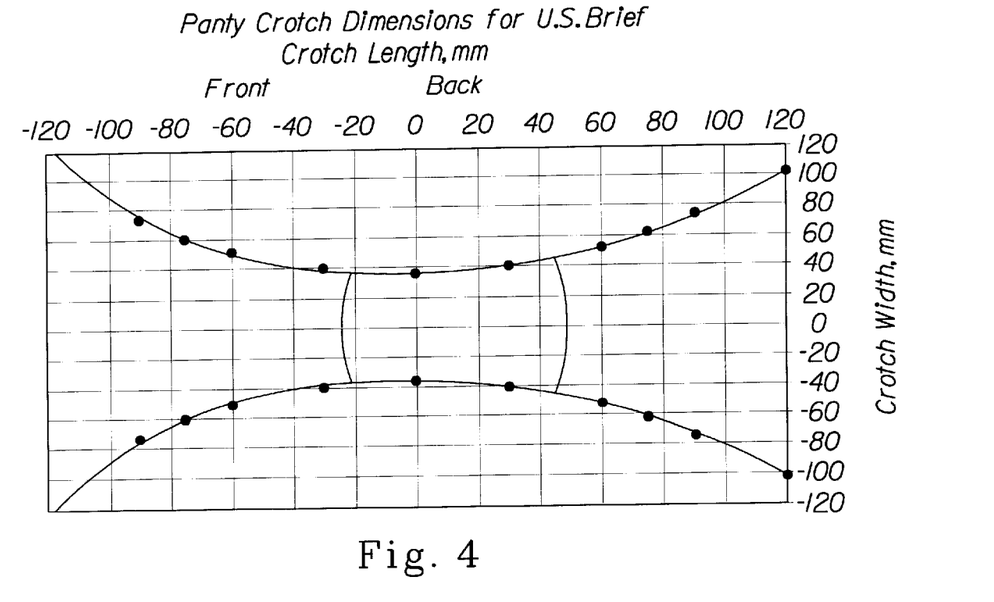
FIGS. 4–7 illustrate average panty crotch dimensions for current varieties of panties marketed in the United States.
Figure 5:
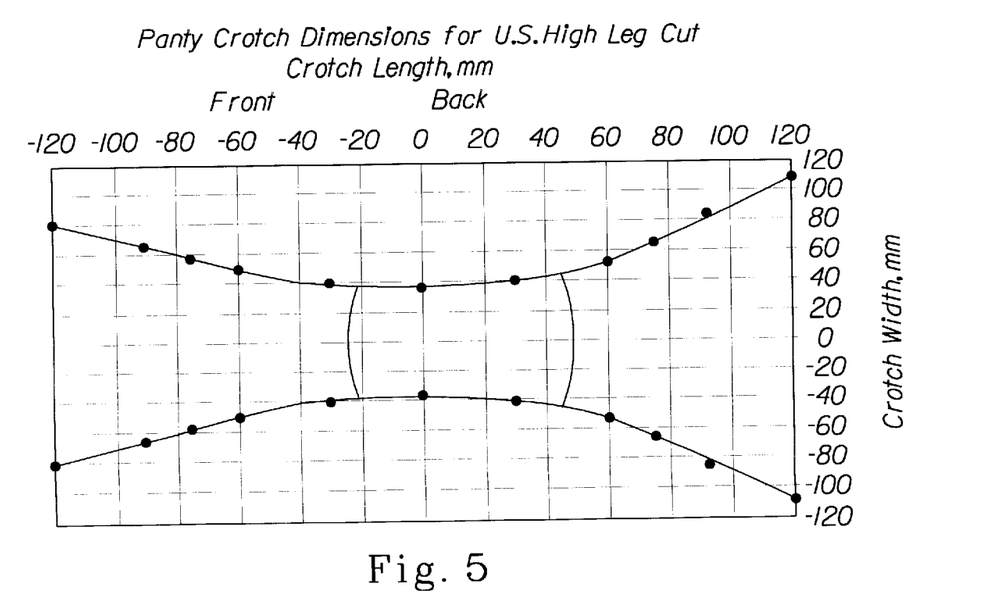
Figure 6:
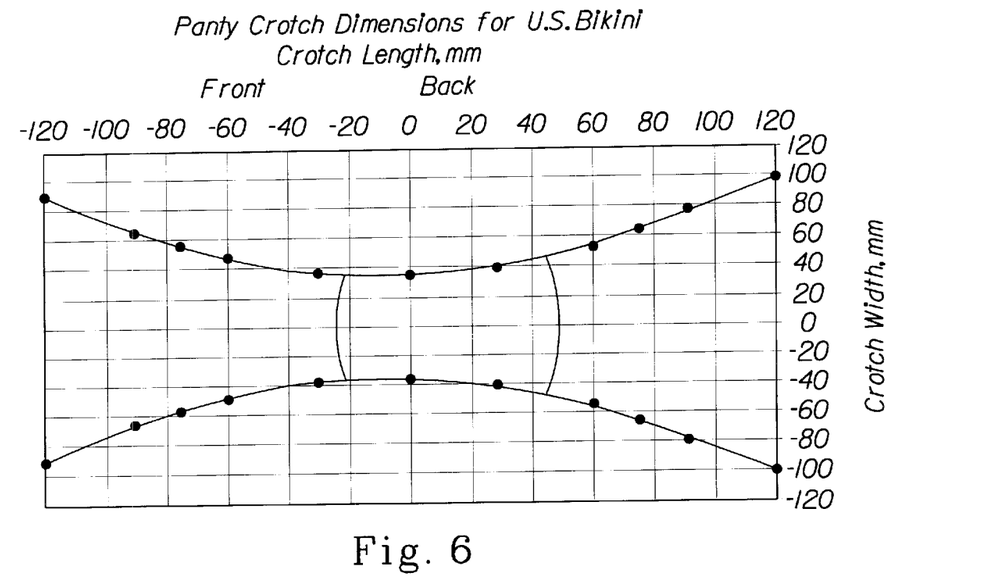
Figure 7:
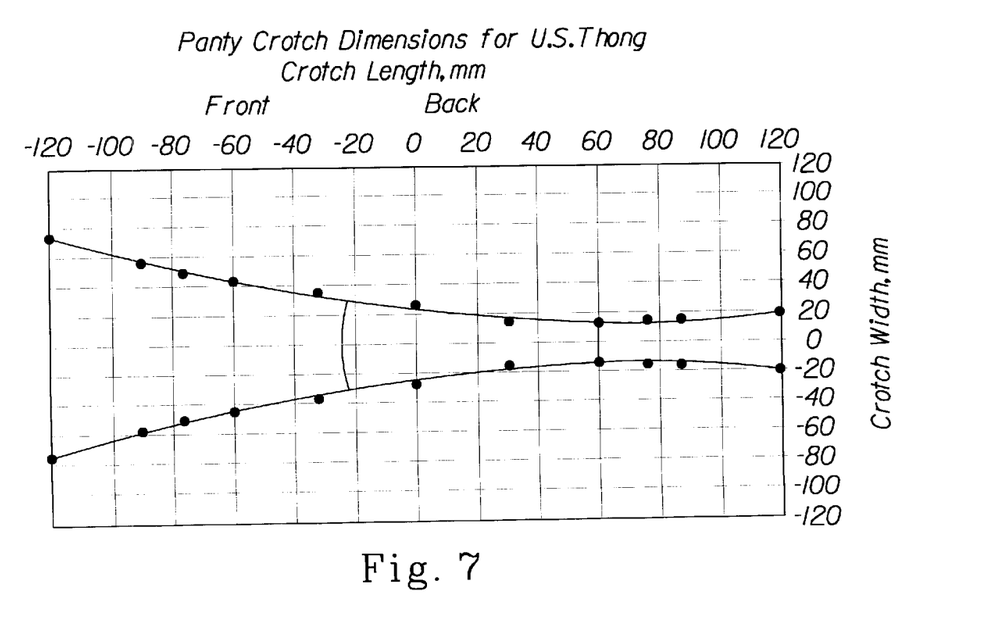

Style A, from the table above, referred to as "thong" style in the U.S., tends to have a high waist and sharply cut leg openings in the front with minimal coverage in the back. Sanitary napkins and panty liners, designed for Style A panties and disclosed in this specification, are designed to be wider in the front and very narrow in the back to accommodate the extremely narrow back configuration of this type of panty. When "wings" are utilized on Style A napkins they are designed to accommodate the very narrow crotch and large leg openings which are typical of this panty style. Referring to FIG. 3, panty "A" illustrates a thong.

Figure 2:
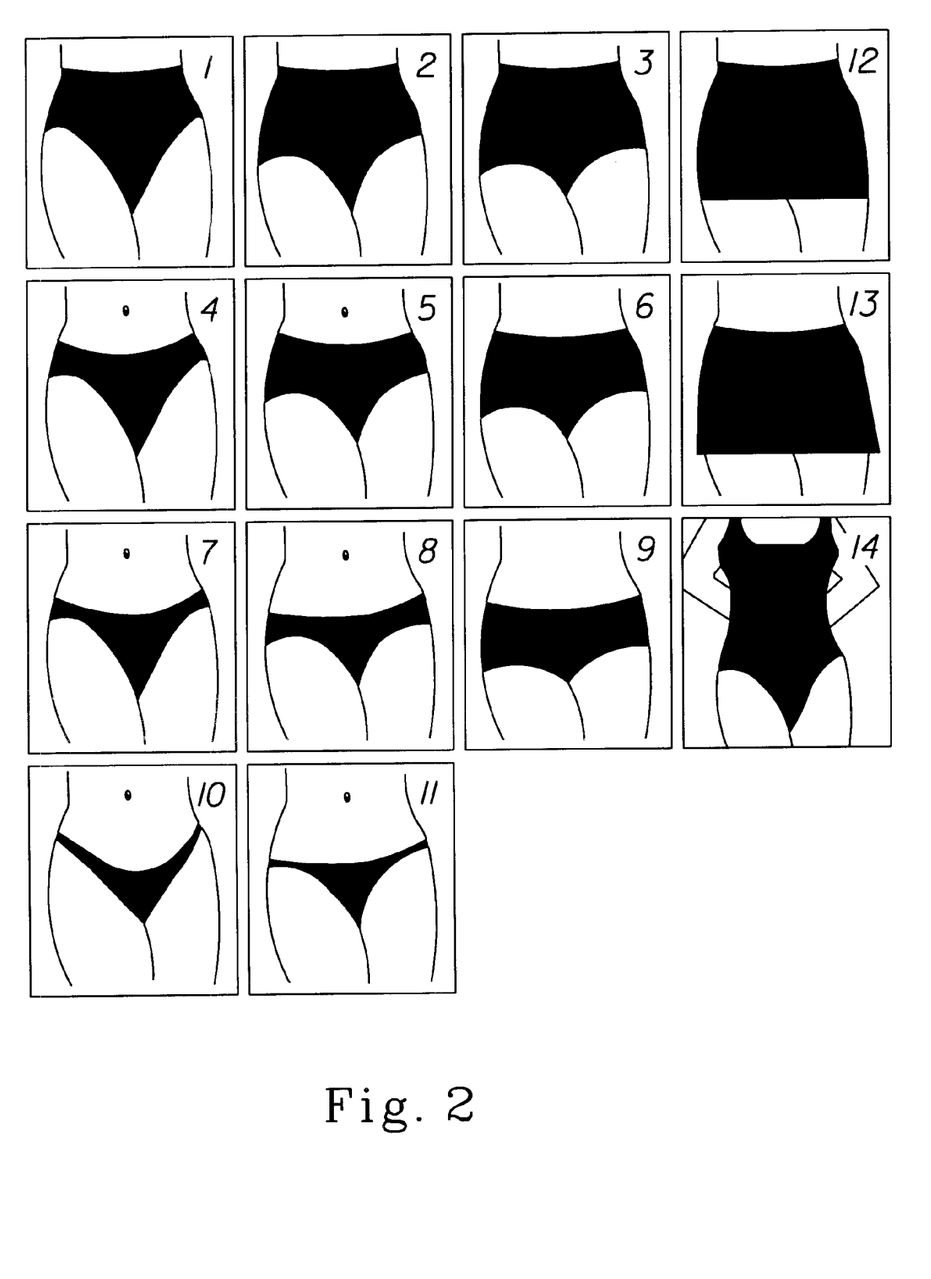
FIG. 2 shows front views of currently marketed panty styles. Panties 1 and 4 are high leg cut (also referred to as "French cut"). Panties 2, 3, and 6 are briefs. Panties 5 and 9 are hipsters. Panties 7 and 8 are bikini panties, while 10 and 11 are a variation referred to as "string bikinis". Panty 12 is referred to as a "modern" or "boy" brief. Panty 13 is a tap pant. Panty 14 is a body suit.

Style B, referred to as "bikini" style in the U.S., tends to have a low rise at the waist and narrow side seams. Examples of Style B panties are illustrated in FIG. 2 as panties 7 and 8. Typically, sanitary napkins designed for Style B panties are shorter and narrower due to the fact that this style is used more frequently by smaller women. As with the napkins designed for Style A panties, wing design is based on crotch contour.

Style C, referred to as "hipster" in the U.S. has a moderate rise and moderate side seams. Examples of Style C panties are shown in FIG. 2 as panties 5 and 9.

Style D, known as "French cut" or "high cut" in the U.S., is characterized by a high rise at the waist and high cut leg openings. Examples of Style D are shown in FIG. 2 as panties 1 and 4. Back views of examples of Style D are illustrated in FIG. 3 as panties D and E. A significant percentage of women of all sizes and ages wear panties of Style D.

Style E panties, which are referred to as "briefs" in the U.S., have the highest rise at the waist and the lowest leg cut openings combined with a wide/symmetrical crotch. Examples of typical Style E panties are shown in FIG. 2 as panties 2, 3, and 6. A back view of a Style E panty is shown in FIG. 3 as panty F. Larger, older women are most likely to wear brief style panties. Feminine hygiene products designed for briefs optimally have front and back core widths, which are essentially symmetrical to follow the panty crotch shape. Such products preferably include a 3dimensional height element to allow the product to be held in closer proximity to the body, since the lower leg cut and high rise tend to locate the panty crotch further away from the body.

As mentioned above, due to the materials and processes now available these sanitary napkin styles have shapes dictated, not by the necessity to place maximum amounts of absorbency in the center of the napkin, but rather by the style of panty preferred by the user. FIGS. 8 through 10 illustrate napkins designed for thong, French cut (also referred to as high cut), and bikini panties. The perimeter of the napkins closely follows the panty perimeter in the crotch areas, those areas of the napkin away from the panty crotch are designed to maximize storage. These new designs, while they vary according to panty style, are typically narrow at the front of the napkin and wider toward the rear. Because of the superior fluid handling abilities of the materials utilized in preferred embodiments of the instant napkins, absorbed fluids are transported away from the site at which they are first deposited onto the napkin to be stored at the ends. Therefore, storage capacity need not be concentrated in the crotch area as in the past.

Absorbent articles comprise an absorbent core, which provides the means for absorbing body fluids, with the optional addition of a topsheet, backsheet, side wrapping elements etc.

Absorbent Core

The absorbent core can comprise any material used in the art for such purpose. Non-limiting examples include natural materials, including comminuted wood pulp, which is generally referred to as airfelt, creped cellulose wadding, hydrogel-forming polymer gelling agents, modified cross-linked cellulose fibers, absorbent foams, absorbent sponges, synthetic staple fibers, polymeric fibers, peat moss or any equivalent material or combinations of materials.

In a preferred embodiment, the absorbent core comprises an absorbent open cell foam. In a more preferred embodiment, the absorbent core comprises an open cell foam of the "High Internal Phase Emulsion" (HIPE) type. In a particularly preferred embodiment, the absorbent core is comprised of a "Thin After Drying" (TAD) HIPE foam absorbent material. Such foam absorbent materials have cells and holes small enough to provide a high capillary absorptive pressure but large enough to prevent or minimize blockage by the insoluble components of blood and blood-based liquids such as menses. This structure provides foam materials capable of absorbing such liquids and then moving these absorbed liquids efficiently to other regions of the foam.

Topsheet

The fluid pervious topsheet, when present, is in close proximity to the skin of the user. The topsheet is preferably as compliant, soft feeling and non-irritating to the user's skin as possible. The topsheet should further exhibit good strikethrough and a reduced tendency to rewet, permitting bodily discharges to rapidly penetrate it and flow toward the core, but not allowing such discharges to flow back through the topsheet to the skin of the wearer. The topsheet is preferably well integrated with the absorbent core, for example, through ultrasonic bonding or commingling of the materials used in the topsheet and the absorbent core.

Backsheet

The backsheet prevents the exudates absorbed and contained in the absorbent core from wetting articles, which contact the sanitary napkin. The backsheet may comprise a woven or nonwoven material, polymeric films such as thermoplastic films of polyethylene or polypropylene, or composite materials such as a film coated nonwoven material. The backsheet is preferably impervious to liquids, but may permit vapors to escape from the absorbent core (i.e. breathable).

Side Wrapping Elements

A preferred feature of the articles of the instant invention is a side wrapping element which varies according to the curve of the perimeter of the crotch area for each panty style. Use and placement of elastics is dependent upon the panty style. FIGS. 8–10 illustrate side wrapping elements which vary by panty type, and are particularly designed for the panty crotch style.

EXAMPLES

An example of a sanitary napkin designed for use with a thong panty is shown in FIG. 8. The front portion of the sanitary napkin 81 is designed to correspond to the front crotch area of the thong. The rear portion of the sanitary napkin 82 is narrower to correspond to the thong's distinctive back. 83 indicates the side wrapping element.

An example of a sanitary napkin designed for use with a bikini panty is shown in FIG. 9. The front portion of the sanitary napkin 91 is designed to correspond to the front crotch area of the panty. The rear portion of the sanitary napkin is indicated as 92. 93 indicates the side wrapping element.

An example of a sanitary napkin designed for use with a high cut panty is shown in FIG. 10. The front portion of the sanitary napkin 101 corresponds to the front crotch area of the panty. The rear portion of the sanitary napkin is indicated as 102. 103 indicates the side wrapping element.

We claim:

1. A method of providing a system of selecting feminine hygiene products to a consumer, comprising the steps of: providing an array of feminine hygiene products from at least one array, wherein said array is comprised of one or more feminine hygiene products and wherein said array is adapted to correspond to a predetermined range of panty styles, and; providing information to said consumer regarding the products which make up said array, thereby enabling said consumer to select feminine hygiene products by panty style.

2. The method according to claim 1, wherein the array additionally corresponds to a predetermined range of one or more of the following: body size, absorbency levels, area coverage and thickness/body fit.

3. The method according to claim 1, wherein the feminine hygiene product is intended for use with a specific panty type selected from the group consisting of thong panties, French cut panties, high leg cut panties, hipsters, bikini panties and briefs.

4. A kit for use in the method of claim 1 comprising:
    a) at least one feminine hygiene product;
    b) a package containing said feminine hygiene product; and
    c) indicia on said package to inform said consumer of a panty style with which said feminine hygiene product is to be used.

5. A kit according to claim 4 additionally comprising a panty.

6. A kit according to claim 4 wherein the indicia are in the form of photographs.

7. A kit according to claim 4 wherein the panty style is selected from the group consisting of: a) thong panties, b) high cut or French cut panties, c) hipster, d) bikini panties and e) briefs.

8. A method of selecting feminine hygiene products by a consumer, comprising the steps of: viewing information regarding at least one array of feminine hygiene products, wherein said array is comprised of one or more feminine hygiene products, and wherein said array is adapted to correspond to a predetermined range of panty styles, and selecting feminine hygiene products by panty style.

9. The method according to claim 8, wherein the array additionally corresponds to a predetermined range of one or more of the following: body size, absorbency levels, area coverage and thickness/body fit.

10. The method according to claim 8, wherein the feminine hygiene product is intended for use with a panty style selected from the group consisting of thong panties, French cut panties, high leg cut panties, hipsters, bikini panties and briefs.

* * * * *